(12) United States Patent
Haworth et al.

(10) Patent No.: US 6,661,228 B2
(45) Date of Patent: Dec. 9, 2003

(54) DATA TRANSFER SYSTEM IN MULTI-SERVER MEDICAL IMAGING SYSTEMS

(75) Inventors: Robert H. Haworth, Brookfield, WI (US); William J. Balloni, Menomonee Falls, WI (US); Mark T. Radick, Muskego, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 426 days.

(21) Appl. No.: 09/746,412

(22) Filed: Dec. 21, 2000

(65) Prior Publication Data

US 2002/0113590 A1 Aug. 22, 2002

Related U.S. Application Data

(63) Continuation-in-part of application No. 09/706,963, filed on Nov. 6, 2000, now Pat. No. 6,348,793.

(51) Int. Cl.[7] .................................................. G01V 3/00
(52) U.S. Cl. ........................................ 324/309; 324/322
(58) Field of Search ................................ 324/309, 307, 324/306, 322, 318, 312, 314, 300

(56) References Cited

U.S. PATENT DOCUMENTS 6,388,687 B1 * 5/2002 Brackett et al. ............. 345/810
6,424,996 B1 * 7/2002 Killcommons et al. ...... 709/206
6,519,632 B1 * 2/2003 Brackett et al. ............. 709/219

* cited by examiner

*Primary Examiner*—Louis Arana
(74) *Attorney, Agent, or Firm*—Quarles & Brady, LLP; Carl Horton

(57) ABSTRACT

A medical imaging system includes a workstation for receiving operator inputs that prescribe a scan and a plurality of servers which control the acquisition of image data and the reconstruction of prescribed images. Tag routers in the workstation and each server enable data in the form of tagged data objects to be exchanged during performance of a scan.

16 Claims, 5 Drawing Sheets

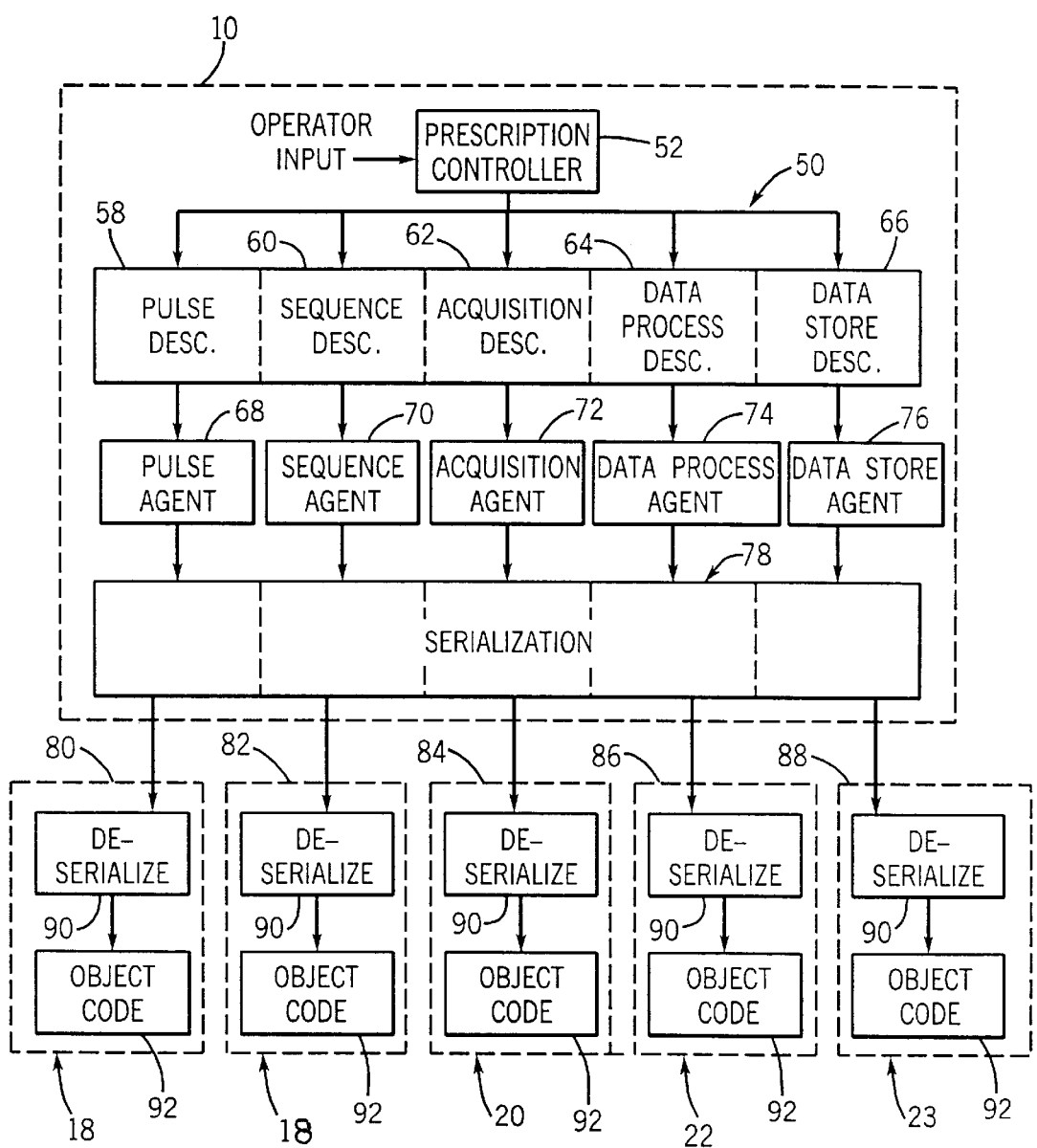

though the workstation 118 and servers 113,
DATA TRANSFER SYSTEM IN MULTI-SERVER MEDICAL IMAGING SYSTEMS

RELATED APPLICATIONS

This is a continuation-in-part application of co-pending U.S. patent application Ser. No. 09/706,963 filed on Nov. 6, 2000 and entitled "System Architecture For Medical Imaging Systems"now U.S. Pat. No. 6,348,793.

BACKGROUND OF THE INVENTION

The field of the invention is medical imaging systems, and particularly, the hardware and software architecture of such systems.

There are many types of medical imaging systems. The primary distinction between the different systems is the medical imaging modality that is used, such as, x-ray, magnetic resonance, ultrasound or nuclear. In addition, a broad range of capabilities and features are typically offered in each imaging modality. For example, a magnetic resonance imaging ("MRI") system may be offered with a range of polarizing magnetic strengths and configurations and with a range of different optional features such as magnetic resonance angiography ("MRA"), cardiac imaging and functional magnetic resonance imaging ("fMRI").

Despite the many differences, medical imaging systems have a number of basic functions in common. All medical imaging systems include an operator interface which enables a particular image acquisition to be prescribed, a data acquisition apparatus which uses one of the imaging modalities to acquire data from the subject, an image reconstruction processor for reconstructing an image using acquired data, and storage apparatus for storing images and associated patient information. Typically, hardware is designed to carry out these functions and software is designed and written for each hardware configuration. When the hardware configuration is changed to take advantage of new concepts or new products, such as faster and more powerful microprocessors, much, if not all, of the software must be rewritten.

Another challenge to the designer of medical imaging equipment is the rapid improvements that are being made in the underlying science for each imaging modality. In magnetic resonance imaging, for example, new pulse sequences and related data acquisition methods are continuously being invented. To add such improvements to an existing MRI system typically requires the rewriting of system software as well as the addition of new, application specific software. The extent of this undertaking depends on the particular improvement being made and the nature of the particular system software architecture in place.

SUMMARY OF THE INVENTION

The present invention is a system architecture for a medical imaging system, and particularly, a system for communicating data between a workstation and a plurality of servers that form the medical imaging system. The communications system includes at the workstation and each server: a router for coupling tag data with the other routers in the system; a tagged data factory for receiving taggable data from a local component, producing a tagged data object from the taggable data, and passing the tagged data object to the local router; and a receiver for registering a local component with the local router and passing tagged data objects received by the local router to the registered component. A component located anywhere in the medical imaging system can register with its local router to receive tagged data objects produced by other processes in the system as scans are being performed. This enables processes to easily couple real-time data with each other without regard to the underlying complexities of serial communications protocols and backplane protocols that may be used by he routers.

BRIEF DESCRIPTION OF THE DRAWINGS

FIG. 3 is a block diagram of functional and data components in the MRI system of FIG. 1 which illustrate a download event;

GENERAL DESCRIPTION OF THE INVENTION

Figure 5:
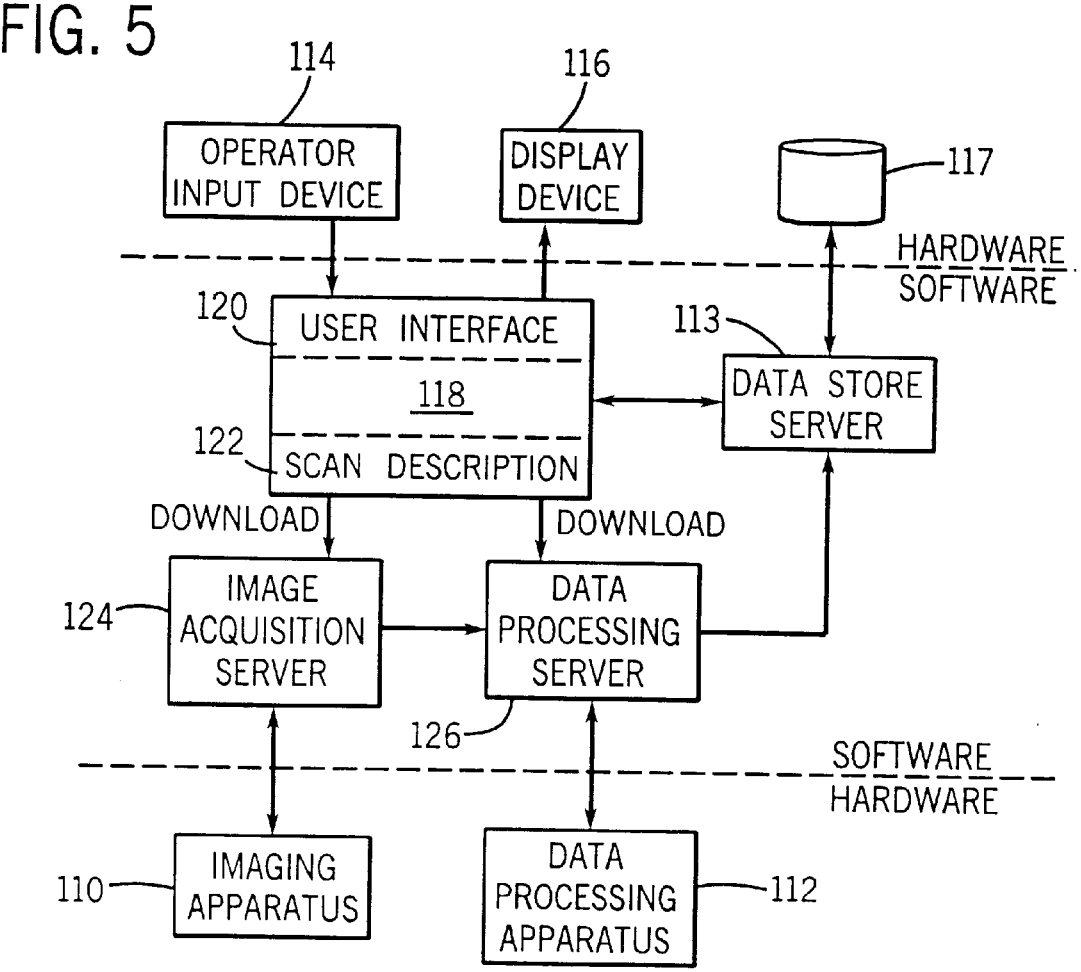
FIG. 5 is a block diagram of an imaging system which employs the present invention.

Referring particularly to FIG. 5, a medical imaging system includes imaging apparatus 110 comprised of mechanical and electrical hardware elements that are operated during a scan to acquire image data. The imaging system also includes data processing apparatus 112 that is operated to reconstruct images using the acquired image data. To operate the system and to enter a scan prescription an operator input device 114, such as a keyboard and control panel, is provided, a display device 116 is provided to present the images for visualization and a storage device 117, such as a hard disc drive, is provided to archive acquired images. The particular imaging modality used, and the complexity and power of these hardware elements varies substantially from one system to the next.

The system includes a workstation 118 which is programmed in a machine independent language, such as Java™, to provide a user interface 120 that enables an operator to enter scan parameters using the operator input device 114. The workstation 118 is programmed to produce a scan description 122, which in its simplest configuration contains image acquisition description components and data processing description components that contain information required by the imaging apparatus 110 and data processing apparatus 112 to perform the prescribed scan.

Prior to run time, a snap shot of the scan description 122 is downloaded to a plurality of servers which control the imaging system hardware apparatus. In the simplest configuration these include an image acquisition server 124 and a data processing server 126 which operate the respective imaging apparatus 110 and data processing apparatus 112. When provided with the scan description components, the servers' programs direct the image system hardware apparatus to perform the prescribed scan. A data store server 113 directs the storage device 117 to save the images along with associated patient information.

The software elements can be easily configured to run on different hardware. The workstation 118 and servers 113, 124 and 126 can run on separate programmable machines, or one or more may run on the same programmable machine. The data processing server 126 or data store server 113 may run on the data processing apparatus 112 or on the workstation 118. Regardless of the configuration, because the workstation 118 is programmed in a machine independent language, it is easily transported to run on different programmable machines. In addition, even though the servers 113, 124 and 126 may be changed to run on different programmable machines, little change is required in the workstation 118 because the scan description can remain unchanged. With changes in servers, the only changes required in the workstation 118 may be minor differences in the particular scan description components that are downloaded to the servers.

The number of servers may also be increased without the need for substantial changes in the workstation 118. For example, if the image acquisition server 124 is split into two or more separate servers, the only substantial change in the workstation 118 is to download the appropriate description components to each server.

The workstation 118 and servers 113, 124 and 126 may be interconnected by backplanes or by serial communications links, or they may reside on the same physical processor. Regardless of the hardware configuration, it is necessary that processes running on these different system elements exchange data during the performance of a scan.

The present invention facilitates such communication of real-time data by providing a tagged data transfer system that enables processes throughout the system to exchange tagged data objects without regard to the complexities of the protocols associated with the underlying backplanes and serial communications links. A key element of this tagged data transfer system is routers located at the workstation 118 and each of the servers 113, 124 and 126. These routers handle the transmission of tagged data between themselves, and enable processes throughout the system to send and receive tagged data without being burdened by the communications details. The processes are thus insulated from particular protocols that may be required to communicate between system components.

DESCRIPTION OF THE PREFERRED EMBODIMENT

Figure 1:
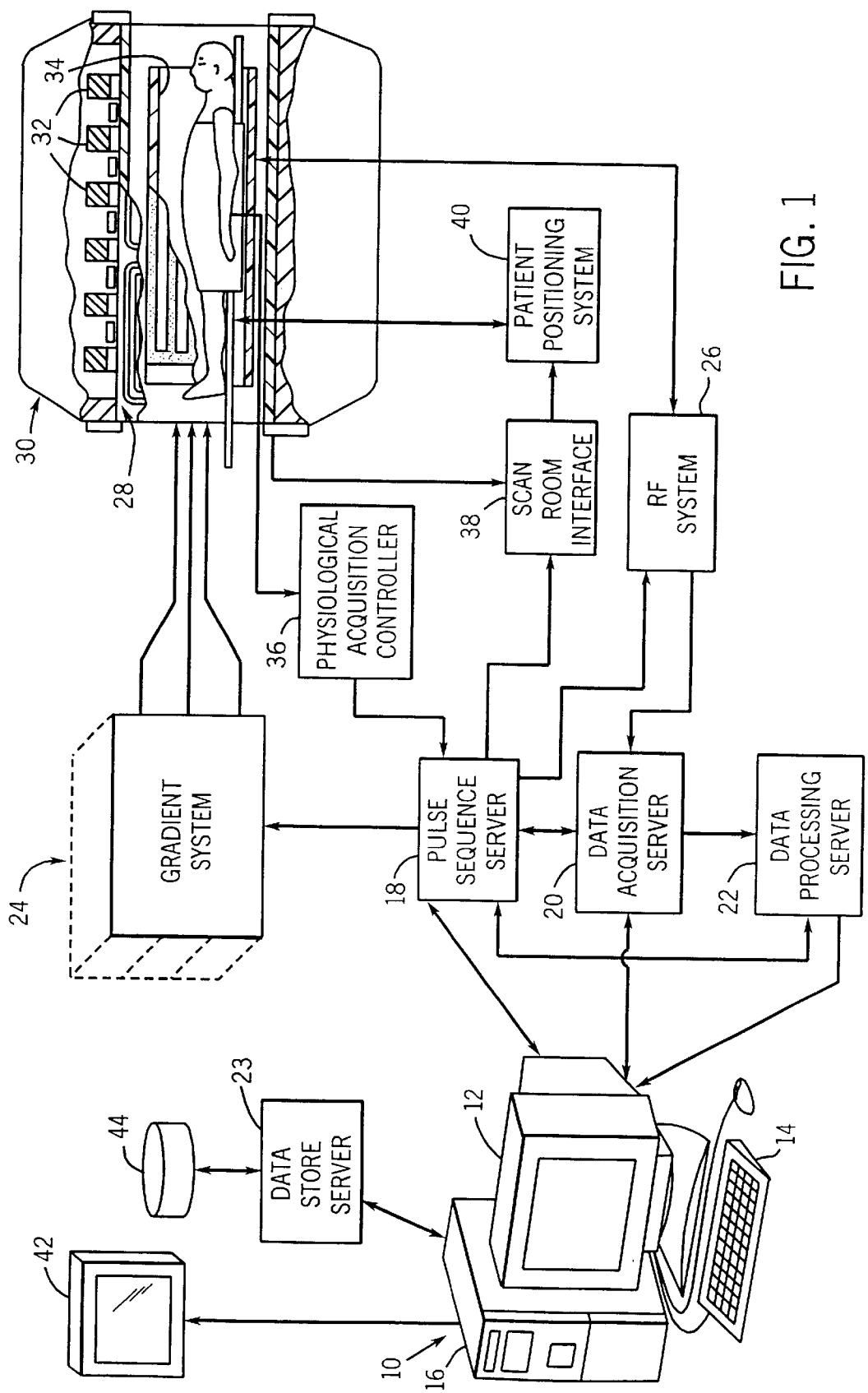
FIG. 1 is a block diagram of an MRI system which employs the preferred embodiment of the invention.

Referring particularly to FIG. 1, the preferred embodiment of the invention is employed in an MRI system. The MRI system includes a workstation 10 having a display 12 and a keyboard 14. The workstation 10 includes a processor 16 which is a programmable machine commercially available from Silicon Graphics, Inc. It is based on a 64-bit microprocessor manufactured by MIPS and it runs the Linux or IRIX™ operating system. The workstation 10 provides the operator interface which enables scan prescriptions to be entered into the MRI system. As will be described in more detail below, the workstation 10 will run one or more Java™ virtual machines which will run code which is programmed in the Java™ language that is fully transportable to any other programmable machine which is Java™ compatible. The programs which implement the operator interface are thus written in a language which is hardware independent. This means that the same Java™ programs can be run on workstations having different hardware configurations and capabilities and they can easily migrate to newer programmable machines that are developed to take advantage of the rapid advances in integrated circuit technology.

The workstation 10 is coupled to four servers: a pulse sequence server 18; a data acquisition server 20; a data processing server 22, and a data store server 23. In the preferred embodiment the data store server 23 is performed by the workstation processor 16 and associated disc drive interface circuitry. The remaining three servers 18, 20 and 22 are performed by separate processors mounted in a single enclosure and interconnected using a 64-bit backplane bus structure based on the PCI standard for industrial and telecommunications applications called "CompactPCI". The pulse sequence server 18 employs a 366 MHz microprocessor model PPC750. The data acquisition server 20 and data processing server 22 both employ the same 366 MHz microprocessor and the data processing server 22 further includes one or more array processors based on parallel vector processors commercially available from Mercury Computer Systems, Inc. as the PowerPC™. Another 366 MHz microprocessor (not shown) serves as a hardware controller on the PCI bus structure and it controls a quad communication controller model MPC860T manufactured by Motorola, Inc.

The workstation 10 and each processor for the servers 18, 20 and 22 are connected to a 100 BaseT Ethernet serial communications network. As will be explained in more detail below, this serial network conveys data that is downloaded to the servers 18, 20 and 22 from the workstation 10 and it conveys tag data that is communicated between the servers and between the workstation and the servers. In addition, a high speed data link using the BIT3 protocol is provided between the data processing server 22 and the workstation 10 in order to convey image data to the data store server 23. Depending on the hardware architecture, some of the servers may be served by a common backplane bus (e.g. PCI), in which case tag data is conveyed to a host processor on the PCI backplane and distributed to the servers on that backplane using the PCI backplane protocol.

The pulse sequence server 18 functions in response to program elements downloaded from the workstation 10 to operate a gradient system 24 and an RF system 26. Gradient waveforms necessary to perform the prescribed scan are produced and applied to the gradient system 24 which excites gradient coils in an assembly 28 to produce the magnetic field gradients $G_x$, $G_y$ and $G_x$ used for position encoding NMR signals. The gradient coil assembly 28 forms part of a magnet assembly 30 which includes a polarizing magnet 32 and an RF coil 34.

RF excitation waveforms are applied to the RF coil 34 by the RF system 26 to perform the prescribed magnetic resonance sequence. Responsive NMR signals detected by the RF coil 34 are received by the RF system 26, amplified, demodulated, filtered and digitized under direction of commands produced by the pulse sequence server 18. Exemplary RF systems are described in U.S. Pat. No. 4,952,877 and U.S. Pat. No. 4,992,736.

The pulse sequence server 18 also optionally receives patient data from a physiological acquisition controller 36. The controller 36 receives signals from a number of different sensors connected to the patient, such as ECG signals from electrodes or respiratory signals from a bellows. Such signals are typically used by the pulse sequence server 18 to synchronize the performance of the scan.

The pulse sequence server 18 also connects to a scan room interface circuit 38 which receives signals from various sensors associated with the condition of the patient and the magnet system. It is also through the scan room interface circuit 38 that a patient positioning system 40 receives commands to move the patient to desired positions during the scan.

It should be apparent that the pulse sequence server 18 performs real-time control of MRI system elements during a scan. As a result, it is necessary that its hardware elements be operated with program instructions that are executed in a timely manner. As will be explained in more detail below, the pulse sequence server 18 is controlled during run-time by programs written in a low level programming language such as assembler, C or C++. The description components for a scan prescription are downloaded from the workstation 10 in the form of objects. The pulse sequence server 18 contains programs which receive these objects using a serialization mechanism. The pulse sequence server 18 also includes a program which converts the objects to C++ objects that are employed by the run-time programs. In the preferred embodiment Java™ objects are downloaded and the Java™ serialization mechanism is employed. The pulse sequence server 18 thus includes both hardware independent programs written in Java™ and hardware dependent programs. It is contemplated that Java™ interpreters will eventually become fast enough that nearly all programs run on the pulse sequence server 18 will be written in hardware independent form.

The digitized NMR signal samples produced by the RF system 26 are received by the data acquisition server 20. The data acquisition server 20 operates in response to description components downloaded from the workstation 10 to receive the real-time NMR data and provide buffer storage such that no data is lost by data overrun. In some scans the data acquisition server 20 does little more than pass the acquired NMR data to the data processor server 22. However, in scans which require information derived from acquired NMR data to control the further performance of the scan, the data acquisition server 20 is programmed to produce such information and convey it to the pulse sequence server 18. For example, during prescans NMR data is acquired and used to calibrate the pulse sequence performed by the pulse sequence server 18. Navigator signals may be acquired during a scan and used to adjust RF or gradient system operating parameters or to control the view order in which k-space is sampled. And, the data acquisition server 20 may be employed to process NMR signals used to detect the arrival of contrast agent in an MRA scan as described in co-pending U.S. patent application Ser. No. 08/635,078 filed Apr. 19, 1996 and entitled "Method For Performing Magnetic Resonance Angiography Using a ContrastAgent". In all these examples the data acquisition server 20 acquires NMR data and processes it in real-time to produce information which is used to control the scan.

As with the pulse sequence server 18, the hardware elements of the data acquisition server 20 are operated at run-time with program instructions in a programming language such as assembler, C or C++. As will be explained in more detail below, the directions for its operation during a scan are downloaded from the workstation 10 in the form of objects. A server receives the objects using the serialization mechanism and the downloaded objects are converted to C++ objects that are employed to operate the data acquisition server 20 during run-time. As indicated above, Java™ objects are downloaded in the preferred embodiment using the Java™ serialization mechanism.

The data processing server 22 receives NMR data from the data acquisition server 20 and processes it in accordance with description components downloaded from the workstation 10. Such processing may include, for example: Fourier transformation of raw k-space NMR data to produce two or three-dimensional images; the application of filters to a reconstructed image; the performance of a backprojection image reconstruction of acquired NMR data; the calculation of functional MR images; the calculation of motion or flow images, etc.

Images reconstructed by the data processing server 22 are conveyed back to the workstation 10 where they are stored. Real-time images are stored in a data base memory cache (not shown) from which they may be output to operator display 12 or a display 42 which is located near the magnet assembly 30 for use by attending physicians. Batch mode images or selected real time images are stored in a host database on disc storage 44. When such images have been reconstructed and transferred to storage, the data processing server 22 notifies the data store server 23 on the workstation 10. The workstation 10 may be used by an operator to archive the images, produce films, or send the images via a network to other facilities.

Directions for the particular operations to be performed by the data processing server 22 are downloaded from the workstation 10 as will be described in more detail below. The time critical functions are performed with programs written in assembler, C or C++ and the downloaded Java™ object directions must be converted to corresponding C++ objects as described above.

Figure 2:
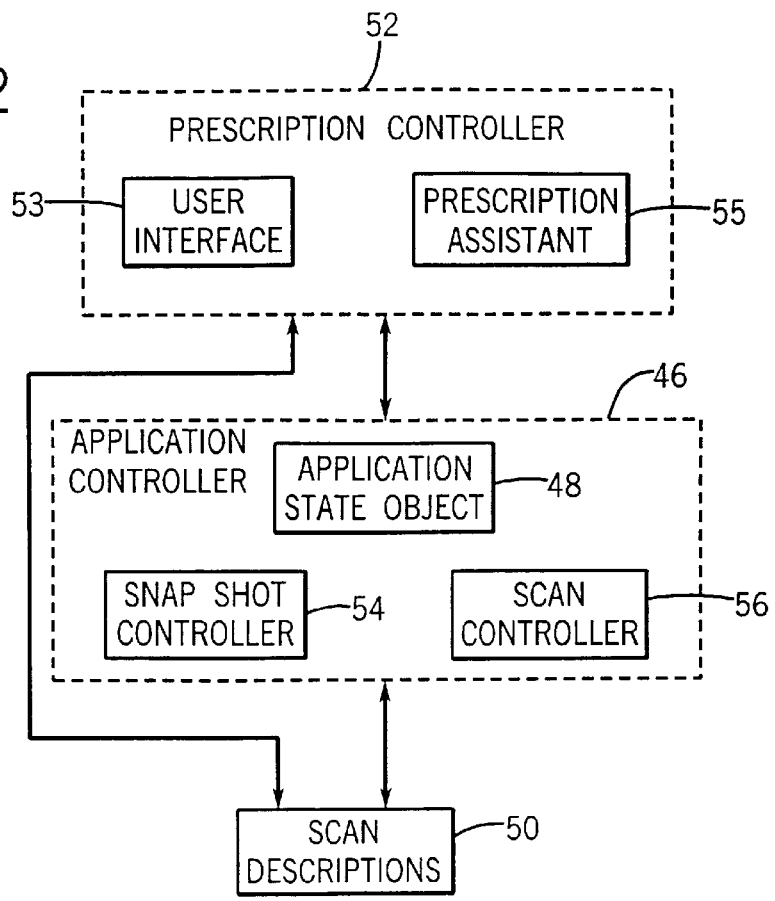
FIG. 2 is a block diagram of functional components in a workstation which forms part of the MRI system of FIG. 1.

As indicated above, the workstation 10 is a Java™ virtual machine which executes programs written in the Java™ programming language. The workstation software is structured to perform "applications" which may be selected and run by an operator. Such applications correspond to clinical imaging procedures and may include, for example:

perform a scan using an FSE pulse sequence;
conduct a CEMRA dynamic study;
perform an fMRI study;
perform a runoff vascular study
perform image post processing
filming
networking An application is a collection of Java™ objects stored in an "application container" that may be selected by an operator to perform a scan. Referring particularly to FIG. 2, each application container includes a Java™ application controller component 46 which directs other Java™ components in the container to perform the scan. These other components include a prescription controller 52 which includes a user interface component 53 and a prescription assistant component 55 that enable an operator to control the procedure performed by the application.

The application container also includes scan descriptions 50. As will be described in more detail below, these scan descriptions are downloaded to the servers 18, 20, 22 and 23 (FIG. 1) and used by those servers to perform the prescribed scan. The stored scan descriptions 50 are unique for every different application, however, further information may be entered by the operator to fully prescribe the scan.

The application controller 46 includes an application state object 48 which maintains the state of the application as the scan is performed. The possible states during a life cycle of an application are as follows:

Initialization
Prescribing
Prescribed
Downloading
Downloaded
Prescanning
Prescanned
Batch Scanning
Real Time Scanning
Scan Paused
Scanned
Reconstructed
Visualized.

This life cycle is driven by commands from the application container (like initialize application), by commands from the operator (like start scan) and by commands generated internally by the application or servers (like scan done).

When the operator selects an application, the application initializes and changes to the "prescribing state" and the prescription controller 52 is enabled to interact with the scan description components 50 to determine what scan parameters must be specified by the operator (e.g. TR, number of slices, location of FOV, flip angle) and determine if the prescription is complete and valid. The prescription controller 52 then signals the application state object 48 to switch to the "prescribed" state and download, prescan and scan buttons on the control panel are enabled.

If the operator hits the "download" button, the application state object 48 changes to the "download state" and the application controller 46 employs a snap shot controller 54 to issue snap shot and download commands. As will be described in more detail below, these commands cause the scan descriptions 50 to be downloaded to the servers 18, 20, 22 and 23. The snap shot controller 54 receives "download done" notification back from each of the servers 18, 20, 22 and 23, and when all four servers have received the snapshots, the application state object 48 is changed to the "downloaded" state.

If the operator hits the scan button, the application state object 48 will change to the scan mode and a scan controller 56 is employed to issue a scan command to the pulse sequence server 18. The next state transition is governed by the scanning mode i.e., real-time or batch. The behavior of the application in the two modes is very different and so there are two different scanning states. If in real-time mode, the application is set to a "real-time scanning" state and if in batch mode, the application state is set to a "batch scanning" state. When in the real-time mode, if the user chooses to pause the scan, the application will transition to a "scan paused" state. If scanning is resumed, the application goes back to the real-time scanning state. In real-time scanning state, the application can be edited and edited descriptions will be downloaded even while the scanning is in progress. However, the application will not make a state transition; instead, the same state will be characterized to allow editing and downloading. It is this behavior of the real-time scanning state that differentiates it from the batch scanning state.

The application will make a transition to the "scanned" state when the operator hits the "stop scan" button. Also, if the application is in the batch scanning mode of operation, the pulse sequence server 18 notifies the application controller 46 when the scan is completed. The application state object changes to the "scanned" state in either event.

When the data processing server 22 completes reconstruction of the acquired images, the data store server 23 is notified and all the images are installed to disk 44. When this task is completed, the application controller 46 is notified and the application state object 48 is changed to the "reconstructed" state. This indicates to the workstation 10 that reconstructed images are available on disk 44 for display or further processing.

Referring particularly to FIG. 3, the scan descriptions 50 contain a set of components that serve to collect scan parameters using the prescription controller 52, and to organize those prescription scan parameters into a set of smaller components that can be downloaded to the servers 18, 20, 22 and 23. On the servers 18, 20, 22 and 23, those downloaded components direct the operation of the hardware in order to carry out the prescribed scan.

There are different description types within each application to provide logical groupings of components to deal with different aspects of executing an MR scan. These description types are:

Pulse Description 58;
Sequence Description 60;
Acquisition Description 62;
Data Processing Description 64;
Data Store Description 66.

The pulse description 58 includes components that define and control the waveforms to be played out on the gradient system and the RF system hardware, along with hardware control components. These components control the dynamic aspects of the waveforms and hardware in response to events produced at run-time by components of the sequence description. This description 58 also includes components that control the filtering of NMR signals received by the RF system 26. These components collectively define a unique set of gradient/RF/control pulses which are used to excite, encode, and readout the NMR signals. Examples are pulse descriptions for 2D spin echo, 2D gradient-echo, 2D fast spin-echo, and 3D gradient-echo sequences.

The sequence description 60 includes a set of components that control the order of pulse sequences played out, and define a series of prescribed events along the scan timeline. These prescribed events defined by the sequence description 60 trigger the dynamic behavior of the pulse components in pulse description 58. These components prescribe a unique acquisition ordering used to define the slice and k-space sampling order. Examples are 2D sequential, 2D interleaved, 3D sequential, 3D elliptical centric, and multi-slice CINE.

The acquisition description 62 includes a set of components that prescribe the real-time processing of NMR signals acquired by the RF system 26. These components direct the performance of operations on acquired NMR signals to produce information that is fed back to components in the sequence description 60 to affect subsequent scanner operation. These components may, for example, process NMR signals during a prescan to feedback changes in the power or frequency of RF pulses produced during the subsequent scan; or process NMR signals to detect when a bolus of contrast agent arrives in a region of interest and trigger the start of a centric view order acquisition; or process "navigator" NMR NMR signals to produce phase correction information which may be used to alter the view order of the scan or alter the demodulation reference frequency of the RF system 26. There are scans commonly used in clinical applications which do not require this capability, however, and in those applications, the components in the acquisition description 62 simply buffer the acquired NMR signals and make them available to the data processing server 22.

The data processing description 64 contains components that direct the data processing server 22 to transform acquired NMR signals into a meaningful form. Image reconstruction is the most common function and the resulting form is a 2D or 3D image of the subject being scanned. Spectroscopy processing can also be defined by these components, in which case the form that results is an image of the spectra of the acquired NMR signals.

The data store description 66 contains components that define the images which are stored in the database during a scan. In addition to the reconstructed images, this may include patient information and scan parameter information which is to appear on the image along with the patient anatomic or spectrographic information.

Referring particularly to FIGS. 2 and 3, after the prescription is completely entered and the scan descriptions 50 are completed, a download may be initiated and the snap shot controller 54 operates to transfer components in the scan descriptions 50 to the servers 18, 20 and 22. This is accomplished by forming agents 68, 70, 72, 74 and 76 from components in the descriptions 58, 60, 62, 64 and 66. Each resulting agent includes a set of objects that can direct the operation of a server to carry out tasks during the scan. To transfer downloadable components to a server, an agent uses serialization indicated at process block 78. Serialization transforms the agent's objects into a stream format that maintains the name of the object class, the instances of their data, and the references between objects. When first initialized, the agent registers with the snap shot controller 54. When the prescription is complete, the snap shot controller 54 informs the agent that it is to take a snap shot. The agent serializes itself and all of its downloadable components, then hands that data stream and the identity of the target server to a snap shot object. That snap shot object is passed to the target server to complete the download.

The serialization mechanism is a standard feature in Java™ which allows objects to be written to an output data stream as described, for example, in U.S. Pat. No. 6,092,120, issued on Jul. 18, 2000 and entitled "Method And Apparatus For Timely Delivery Of A Byte Code And Serialized Object" which is incorporated herein by reference. The data stream can be passed across process boundaries, or saved to disk to retain the state of the objects for later use. The serialized object data stream carries the class name of each object and that object's instance data described by attribute name, type, and value. A powerful aspect of serialization is the ability to capture the relationships between objects when the data stream is received and deserialized. This allows a graph of objects to be captured in the serialized stream and then recreated at a later time or on a different machine. The serialization mechanism captures all relationships between objects. Each object in the graph is only serialized once. Should one object be referenced more than one time, the serialization mechanism recognizes the repeat and inserts a reference to the previous occurrence in the stream. This prevents endless loops during serialization and the potential for stream bloat due to duplication of objects. It is important to note that the serialized data stream only contains the object data and does not include object method code, the executable portion of the object. This substantially reduces the amount of data downloaded to the servers by the snap shot controller 54. It also requires that object method code be resident on each server.

Referring particularly to FIG. 3, the serialized agents 68, 70, 72, 74 and 76 are downloaded to functional servers 80, 84, 86 and 88. Functional servers 80, 84 and 86 reside on the three servers 18, 20 and 22 and the data is conveyed through an Ethernet serial communications network. The pulse sequence server 80 resides on the pulse sequence server hardware 18, the acquisition server 84 resides on the data acquisition server hardware 20, and the data processing server 86 resides on server hardware 20 or 22. The data store server 88 resides on the workstation 10. It should be apparent to those skilled in the art that the functional servers may reside on many different hardware combinations and that the present architecture facilitates the use of different hardware combinations. If different server hardware is used, the only change required in the workstation software is the agent which groups description components specifically targeted for the new server hardware. The new agent is constructed using components in the existing scan descriptions 50 and it is created and downloaded using existing software as described above.

The serialized agents are received by the corresponding target functional servers when a snap shot download event is generated by the snap shot controller 54. Each stream of serialized agents must be deserialized as indicated at process blocks 90. If the servers are written in Java™, this deserialization is a standard feature of the language as described, for example in the above cited U.S. Pat. No. 6,092,120. As indicated above, however, in the preferred embodiment the servers employ C++ object code and the deserialization requires some extra effort. To perform the deserialization the servers use a software product created by Rogue Wave Software, Inc. of Boulder Colo. This product provides a C++ library for restoration of the Java™ object stream. This tool is able to parse the Java™ stream and present the contained class names, attributes, and object relationships to reader writer classes. Each C++ component that is to be created from the stream must have a reader writer. This class maps the parsed information to appropriate constructors and set methods of the C++ objects.

As stated previously, the serialized stream does not contain code, only instance data for the objects. The code for the C++ classes resides on the server. Every type of Java™ agent and Java™ downloadable component has a mirror C++ object on the server. The mirrored components must have the same class name and share a common set of attributes. At the completion of the deserialization process, executable object code indicated at 92 resides in each of the functional servers 80, 84, 86 and 88. Each functional server does the equivalent of signaling the snap shot controller 54 in the workstation 10 when the download is completed and the application state object 48 changes to the "downloaded" state upon receiving a signal from every server.

When the operator hits the "run" button on the control panel, the scan controller 56 coordinates the run time operation of the workstation and the servers to perform the scan. To do this, the scan controller 56 may communicate with the functional servers 80, 84, 86 and 88 across a number of different bus structures, backplanes and serial communications networks. For example, the scan controller 56 signals the pulse sequence server 18 to start the scan, and it receives a notice from the data processing server 22 when images are available to view. In addition, the functional servers must communicate with each other during the scan. For example, the acquisition server 84 may send information back to server 80 to alter a pulse or the sequence during the scan. Image data acquired by the acquisition server 84 is passed on to the data processing server 86 and the data store server 88 receives information from both the data processing server 86 and the workstation 10 to carry out its function of merging patient information with reconstructed images.

This run-time communications is provided by a tagged data transfer system. Tagged data transfer is a system that isolates applications/servers from hardware dependencies by providing tag (data packet) representation and routing mechanisms with different low level communication schemes. A tagged data packet consists of a header and a payload. The header contains information useful for interpreting the payload such as Id, Tagged Data Type, Payload Size, Byte Order, Hop Count, etc. The Payload contains the platform independent data or tagged data object. The data being passed can be transferred and interpreted in-process or inter-process including processes distributed across different programmable machines.

Tagged Data:

Header
Id
Type
PayloadSize
ByteOrder

PayLoad

Figure 4:
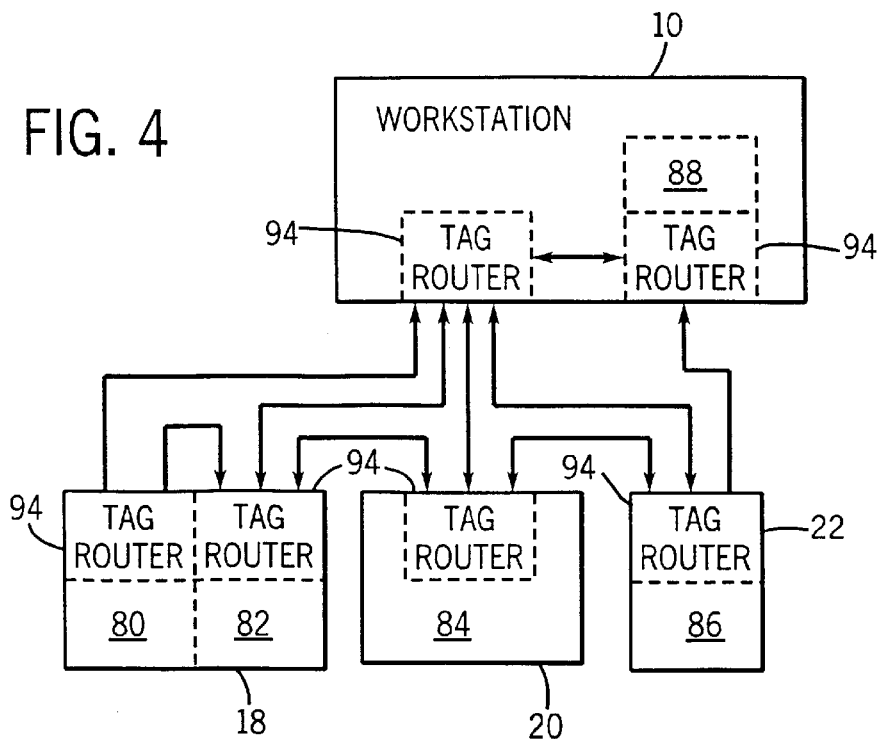
FIG. 4 is a block diagram of elements in the MRI system of FIG. 1 which illustrate the tag communication system.

As shown in FIG. 4, the workstation 10 and each of the functional 10 servers 80, 84, 86 and 88 includes a tag router 94. These are written in Java™ and in C++ and they communicate with each other using the available communications hardware and protocols. Any component interested in receiving tagged data has a logical address which it registers with its local tag router. Each process has at least one tag router which enables tagged data transfer with other components and processes.

Figure 6:
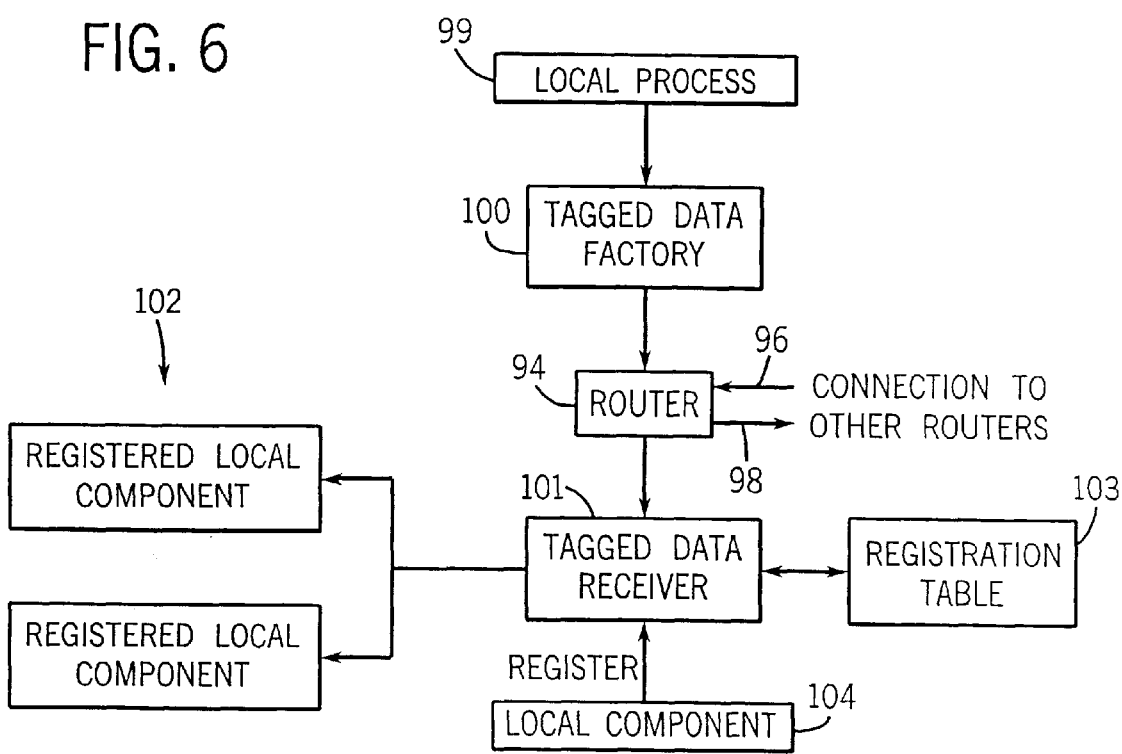
FIG. 6 is a block diagram of the tag communications system elements associated with each router in FIG. 4.

Referring particularly to FIG. 6, each tag router 94 maintains data transfer channels which resemble stream pipes. These channels hide the low level communication details from the tag router 94 and provide a mechanism to transport tagged data to its peer in another process space. A channel consists of an incoming data channel 96 and an outgoing data channel 98. A sending component has the option of getting notification upon the failure or success of the tag send operation.

The DICOM standard is used to represent data and hence achieve platform independence. The Digital Imaging and Communications in Medicine standard was developed by the American College of Radiology and the National Electrical Manufacturers Association to provide a standard for transferring medical images and associated information between devices. The data types in DICOM are well defined, and are hardware independent. Predefined DICOM tags can be used to identify data that is being transmitted and packets can be easily extended by application programmers. The data types supported are a subset of those specified by the DICOM specification, including string, integer, and floating point.

Referring still to FIG. 6, tagged data objects are created by a local process 99 requesting a tagged data system singleton from a tagged data factory 100. The data to be transported is passed to the tagged data factory 100 in the form of a taggable. The tagged data factory 100 produces a tagged data object by adding a header, and the object is sent to the tag router 94. The router 94 takes care of sending the tagged data object to its destination.

Associated with each router 94 is a tagged data receiver 101 which receives tagged data objects from the router 94 and passes them on to registered local components 102. The tagged data receiver 101 employs a registration table 103 which indicates the logical addresses of the local components 102 which are registered to receive tagged data objects along with the types of data objects those components are registered to receive. An unregistered local component such as that indicated at 104 may register with the tagged data receiver by identifying its logical address and indicating the types of tagged objects (e.g. reconstruction done, image installation done, raw data frame characteristics, or image geometry characteristics) it wants to receive.

Registered components 102 are thus passed tagged data objects that are specifically sent to them by other components and processes located anywhere in the system and they are passed tagged data objects of specified types. Thus, registered components 102 anywhere in the system can monitor tagged data objects of specified types which are passed from one process to another anywhere in the system.

Referring particularly to FIG. 4, in the context of a medical imaging system, the tagged data transfer system enables the real-time monitoring of the scan. Tagged data passed between the pulse sequence server 18 and the data acquisition server 20 and between the data acquisition server 20 and the data processing server 22 may be monitored by a process in the workstation 10. This workstation process may, for example, use that data to produce a real-time display for the operator which indicates the progress of the scan.

What is claimed is:

1. In a medical imaging system having a workstation and a plurality of servers, a tagged data system which comprises:
    a set of routers located at respective servers and the workstation for coupling tag data therebetween, each router including:
    a) a tagged data factory for receiving taggable data from a local process and producing a tagged data object, and for passing the tagged data object to the router for transmission to another router; and
    b) a tagged data receiver for registering with the router a local process and for passing to registered local processes tagged data objects received by the router from other routers.

2. The medical imaging system as recited in claim 1 in which the system is a magnetic resonance imaging system in which one of the servers is a pulse sequence server.

3. The medical imaging system as recited in claim 2 in which other ones of the servers include a data acquisition server and a data processing server.

4. The medical imaging system as recited in claim 1 in which the tagged objects each include a header and a payload and the header includes a field indicative of the type of data contained in the payload.

5. The medical imaging system as recited in claim 4 in which the tagged data receiver includes a table which stores an indication of the type of tagged data objects to be passed to a registered local component.

6. The medical imaging system as recited in claim 5 in which the table stores the logical address of each registered local component.

7. The medical imaging system as recited in claim 4 in which the payload is data which conforms to a subset of a Digital Imaging and Communications in Medicine (DICOM) standard.

8. A magnetic resonance imaging (MRI) system which comprises:
    a) a workstation programmed to provide:
        i) an operator interface for receiving input information which prescribes a scan to be performed;
        ii) a pulse description comprised of components which determine the pulses produced during the scan;
        iii) a sequence description comprised of components which determine the pulse sequence used during the scan to acquire NMR signals;
        iv) a data processing description comprised of components which determine how the acquired NMR signals are processed into a clinically useful form;
    b) a plurality of servers coupled to the workstation and being operable to receive the descriptions downloaded from the workstation, each server being operable in response to downloaded descriptions to operate elements of the MRI system to perform the scan; and
    c) a tagged data system comprised of routers located at the workstation and each of the servers, the routers being coupled together to convey tagged data objects therebetween and each router being operable to produce tagged data objects from data passed to the router from a local process and being operable to pass received tagged data objects to a registered local process.

9. The MRI system as recited in claim 8 in which one of the servers controls a gradient system and an RF system on the MRI system.

10. The MRI system as recited in claim 9 in which another one of the servers reconstructs images from NMR signals produced by the RF system.

11. The MRI system as recited in claim 10 in which the workstation resides on one programmable machine, the one server resides on a second programmable machine, and the other one of the servers resides on a third programmable machine.

12. The MRI system as recited in claim 8 in which each router includes:
    a) a tagged data factory for receiving taggable data from a local process and producing a tagged data object, and for passing the tagged data object to the router for transmission to another router;
    b) a tagged data receiver for registering with the router a local process and for passing to registered local processes tagged data objects received by the router from other routers.

13. The medical imaging system as recited in claim 12 in which the tagged objects each include a header and a payload and the header includes a field indicative of the type of data contained in the payload.

14. The medical imaging system as recited in claim 13 in which the tagged data receiver includes a table which stores an indication of the type of tagged data objects to be passed to a registered local process.

15. The medical imaging system as recited in claim 14 in which the table stores the logical address of each registered local process.

16. The medical imaging system as recited in claim 13 in which the payload is data which conforms to a Digital Imaging and Communications in Medicine (DICOM) standard.

* * * * *